(12) United States Patent
Belsick et al.

(10) Patent No.: US 10,302,595 B2
(45) Date of Patent: *May 28, 2019

(54) ACOUSTIC RESONATOR DEVICES AND FABRICATION METHODS PROVIDING HERMETICITY AND SURFACE FUNCTIONALIZATION

(71) Applicant: Qorvo US, Inc., Greensboro, NC (US)

(72) Inventors: John Belsick, Bend, OR (US); Rick Morton, Bend, OR (US); Matthew Ryder, Bend, OR (US)

(73) Assignee: QORVO US, INC., Greensboro, NC (US)

( * ) Notice: Subject to any disclaimer, the term of this patent is extended or adjusted under 35 U.S.C. 154(b) by 212 days.

This patent is subject to a terminal disclaimer.

(21) Appl. No.: 15/334,528

(22) Filed: Oct. 26, 2016

(65) Prior Publication Data

US 2017/0134001 A1 May 11, 2017

Related U.S. Application Data

(60) Provisional application No. 62/252,402, filed on Nov. 6, 2015.

(51) Int. Cl.
*H03H 9/02* (2006.01)
*G01N 29/02* (2006.01)
(Continued)

(52) U.S. Cl.
CPC ......... *G01N 29/022* (2013.01); *G01N 29/222* (2013.01); *G01N 29/2437* (2013.01);
(Continued)

(58) Field of Classification Search
CPC .................................................. H03H 9/02023
(Continued)

(56) References Cited

U.S. PATENT DOCUMENTS

| 4,640,756 A | 2/1987 | Wang et al. |
| 6,320,295 B1 | 11/2001 | McGill et al. |

(Continued)

FOREIGN PATENT DOCUMENTS

| EP | 2 204 641 A1 | 7/2010 |
| WO | WO 2006/063437 A1 | 6/2006 |
| WO | WO 2007/123539 A1 | 11/2007 |

OTHER PUBLICATIONS

U.S. Appl. No. 15/293,063, filed Oct. 13, 2016, McCarron et al.
(Continued)

*Primary Examiner* — Joseph Chang
(74) *Attorney, Agent, or Firm* — Mueting, Raasch & Gebhardt, P.A.

(57) ABSTRACT

A micro-electrical-mechanical system (MEMS) resonator device includes a top side electrode overlaid with a low water permeability hermeticity layer and an interface layer including a material (e.g., gold or a hydroxylated oxide surface) suitable for receiving a self-assembled monolayer (SAM) that may be functionalized with a functionalization (e.g., specific binding) material, with the foregoing layers being designed to have insubstantial impact on sensor performance. Atomic layer deposition may be used for deposition of the hermeticity and/or interface layers. The hermeticity layer protects the electrode material from attack in corrosive liquid environments, and the interface layer facilitates proper chemical binding of the SAM. Sensors and microfluidic devices incorporating MEMS resonator devices are also provided.

20 Claims, 6 Drawing Sheets

(51) Int. Cl.
  *G01N 29/22* (2006.01)
  *G01N 29/24* (2006.01)
  *H03H 9/17* (2006.01)
(52) U.S. Cl.
  CPC .. *G01N 2291/012* (2013.01); *G01N 2291/014* (2013.01); *G01N 2291/015* (2013.01); *G01N 2291/0255* (2013.01); *G01N 2291/0256* (2013.01); *G01N 2291/0426* (2013.01); *H03H 9/175* (2013.01)
(58) Field of Classification Search
  USPC .......................................................... 331/154
  See application file for complete search history.

(56) References Cited

U.S. PATENT DOCUMENTS

| | | | |
|---|---|---|---|
| 7,468,608 B2 | 12/2008 | Feucht et al. | |
| 8,409,875 B2 | 4/2013 | Johal et al. | |
| 8,448,494 B2 | 5/2013 | Mastromatteo et al. | |
| 2005/0148065 A1* | 7/2005 | Zhang ................... | B82Y 15/00 435/287.2 |
| 2006/0125489 A1 | 6/2006 | Feucht et al. | |
| 2007/0210349 A1 | 9/2007 | Lu et al. | |
| 2011/0121916 A1* | 5/2011 | Barber ..................... | H03H 3/04 333/187 |
| 2012/0280758 A1* | 11/2012 | Jaakkola ................ | H01P 7/082 331/154 |
| 2012/0319790 A1* | 12/2012 | Nakamura ......... | H03H 9/02259 331/154 |
| 2013/0063227 A1* | 3/2013 | Burak .................... | H03H 9/131 333/187 |
| 2015/0293060 A1 | 10/2015 | Jacobsen | |
| 2017/0110300 A1 | 4/2017 | Mccarron et al. | |
| 2017/0117871 A1 | 4/2017 | Rivas et al. | |
| 2018/0034438 A1 | 2/2018 | Ryder et al. | |
| 2018/0048280 A1 | 2/2018 | Ryder et al. | |

OTHER PUBLICATIONS

U.S. Appl. No. 15/334,511, filed Oct. 26, 2016, Rivas et al.
U.S. Appl. No. 15/334,459, filed Oct. 26, 2016, Ryder et al.
U.S. Appl. No. 15/334,482, filed Oct. 26, 2016, Ryder et al.
U.S. Appl. No. 62/246,302, filed Oct. 26, 2015, Rivas et al.
U.S. Appl. No. 62/367,211, filed Jul. 27, 2016, Ryder et al.
U.S. Appl. No. 62/373,668, filed Aug. 11, 2016, Ryder et al.
PCT/US2016/058749, filed Oct. 26, 2016, Qorvo US, Inc.
International Patent Application No. PCT/US2016/058745, filed Oct. 26, 2016; International Search Report / Written Opinion dated Feb. 1, 2017; 13 pages.
International Patent Application No. PCT/US2016/058749; filed Oct. 26, 2016; International Search Report / Written Opinion dated Apr. 20, 2017; 16 pages.
Brand, et al., "Resonant MEMS: Fundamentals, Implementation and Application", *Advanced Micro & Nanosystems*, series ed. Brand, et al., 2015. John Wiley & Sons, Inc., pp. 370-371.
Chen, et al., "The Liquid Sensor Using Thin Film Bulk Acoustic Resonator with C-Axis Tilted AlN Films"; 2013, *Journal of Nanomaterials*, vol. 2013, Article ID 245095, 8 pages.
Choi, et al., "A regenerative biosensing surface in microfluidics using electrochemical desorption of short-chain self-assembled monolayer", 2009, *Microfluidics and Nanofluidics*, Springer-Verlag, 7(6): 9 pages. Published online Apr. 10, 2009.
Ferrari, et al., Chapter 2, "Overview of Acoustic-Wave Microsensors", *Piezoelectric Transducers and Applications*, Springer-Verlag, Berlin Heidelberg, 2008, pp. 39-62.
Garcia-Gancedo, et al., "AlN-based BAW resonators with CNT electrodes for gravimetric biosensing"; Dec. 15, 2011, *Sensors and Actuators B: Chemical*, 160(1):1386-1393.

Glass, et al., "Organosilane deposition for microfluidic applications", 2011, *Biomicrofluidics*, 5(3):036501-1 to 036501-7. Published online Aug. 16, 2011.
Hohmann, et al., "Surface Acoustic Wave (SAW) Resonators for Monitoring Conditioning Film Formation", 2015, *Sensors*, 15(5):11873-11888. Published online May 21, 2015.
Jiang; et al., "Electrochemical Desorption of Self-Assembled Monolayers Noninvasively Releases Patterned Cells from Geornettical Confinements", Nov. 26, 2002, *J. Am. Chem. Soc.*, 2003(125):2366-2367.
Länge, et al., "Surface acoustic wave biosensors: a review", 2008, *Analytical and Bioanalytical Chemistry*, 391:1509-1519. Published online Feb. 12, 2008.
Mecca, "From Quartz Crystal Microbalance to Fundamental Principles of Mass Measurements", 2005, *Analytical Letters*, 38:753-767.
Montagut, et al., Chapter 9, "QCM Technologyin Biosensors", *Biosensors—Emerging Materials and Applications*, Serra, ed., Jul. 18, 2011, Intech Open Access Publisher, pp. 153-178.
Onen, et al., "Surface Modification on Acoustic Wave Biosensors for Enhanced Specificity," 2012, *Sensors*, 12(9):12317-12328, Published online Sep. 10, 2012.
Plueddemann, *Silane Coupling Agents*, Springer Science+Business Media, New York, New York, 1991, p. 31.
Tencer, et al., "A contact angle and ToF-SIMS study of SAM-thiol interactions on polycrystalline gold", Feb. 15, 2011, *Applied Surface Science*, 257(9):4038-4043. Published online Dec. 4, 2010.
Villa-López, et al "Design and modelling of solidly mounted resonators for low-cost particle sensing", 2016, *Measurement Science and Technology*, 27(2): 13 pages. Published online Dec. 15, 2015.
Voiculescu, et al., "Acoustic wave based MEMS devices for biosensing applications", 2012, *Biosensors and Bioelectronics*, 33:1-9. Published online Jan. 16, 2012.
Ward, et al., "Radial Mass Sensitivity of the Quartz Crystal Microbalance in Liquid Media", May 1, 1991, *Analytical Chemistry*, 63(9):886-890.
Willey, et al., "Rapid Degeneration of Alkanethiol-Based Self-Assembled Monolayers on Gold in Ambient Laboratory Conditions", Aug. 3, 2004, *Surface Science*, Preprint submitted to Elsevier Science, 576(1): 23 pages.
Wingqvist, et al., "Shear mode AlN thin film electro-acoustic resonant sensor operation in viscous media", 2007, *Sensors and Actuators B*, 123:466-473. Published online Nov. 2, 2006.
Ye, et al., "Photoreactivity of Alkysiloxane Self-Assembled Monolayers on Silicon Oxide Surfaces", 2001, *Langmuir*, 1 7(15):4497-4500. Published online Jun. 21, 2001.
Yuan, et al., "A Method for Removing Self-Assembled Monolayers on Gold", 2008, *Langmuir*, 24(16):8707-8710. Published online Jun. 27, 2008.
Zhang, et al., "Excimer laser ablation of thin gold films on a quartz crystal microbalance at various argon background pressures", Jun. 1997, *Applied Physics A*, 64(6):545-552.
Zhang, et al., "A single-chip biosensing platform integrating FBAR sensor with digital microfluidic device", *2014 IEEE International Ultrasonics Symposium Proceedings*, 2014, 3 pages.
Zhou, et al., "Interfacial Structures and Properties of Organic Matetials for Biosensors: An Overview", 2012, *Sensors*, 12:15036-15062. Published online Nov. 6, 2012.
Qorvo US, Inc., "Summary of Sales Activity of Predecessor to Applicant Concerning Tilted C-Axis Aluminum Nitride Products," Unpublished, Jan. 10, 2017, 1 page.
Bjurström, J. et al., "Design and Fabrication of Temperature Compensated Liquid FBAR Sensors," IEEE Ultrasonics Symposium, Oct. 2-6, 2006, pp. 894-897.
Canaria, Christie A. et al., "Formation and removal of alkylthiolate self-assembled monolayers on gold in aqueous solutions," Lab on a Chip, vol. 6, No. 2, 2006, pp. 289-295.
Corso, Christopher et al., "Development of a Simple Inexpensive Bulk Acoustic Wave (BAW) Nanosensor for cancer Biomarkers: Detection of Secreted Sonic Hedgehog from Prostate Cancer Cells," Abstract #8866, Winship Cancer Institute, Emory University, Georgia Institute of Technology, Oct. 2012, 1 page.

(56) References Cited

OTHER PUBLICATIONS

Groner, M. D. et al., "Gas diffusion barriers on polymers using $Al_2O_3$ atomic layer deposition," Applied Physics Letters, vol. 88, Jan. 31, 2006, pp. 051907-1 to 051907-3.

Link, Mathias, "Study and realization of shear wave mode solidly mounted film bulk acoustic resonators (FBAR) made of c-axis inclined zinc oxide (ZnO) thin films: application as gravimetric sensors in liquid environments," Université Henri Poincaré —Nancy I, Thesis, Sep. 14, 2006, 225 pages.

Love, J. Christopher et al., "Self-Assembled Monolayers of Thiolates on Metals as a Form of Nanotechnology," Chemical Reviews, vol. 105, No. 4, Mar. 25, 2005, pp. 1103-1169.

Luo, J. K. et al., "Acoustic Wave Based Microfluidics and Lab-on-a-Chip," Modeling and Measurement Methods for Acoustic Waves and for Acoustic Microdevices, Chapter 21, Aug. 28, 2013, InTech, pp. 515-556.

Mehdizadeh, Emad et al., "Microelectromechanical disk resonators for direct detection of liquid-phase analytes," Sensors and Actuators A: Physical, vol. 216, Sep. 1, 2014, pp. 136-141.

Meyer, Jens et al., "$Al_2O_3/ZrO_2$ Nanolaminates as Ultrahigh Gas-Diffusion Barriers—A Strategy for Reliable Encapsulation of Organic Electronics," Advanced Materials, vol. 21, 2009, pp. 1845-1849.

Milyutin, Evgeny, "Theoretical and Experimental Study of Piezoelectric Modulated AlN Thin Films for Shear Mode BAW Resonators," EPFL, Thesis No. 5113, Nov. 4, 2011, 109 pages.

Mooney, J.F. et al., "Patterning of functional antibodies and other proteins by photolithography of silane monolayers," Proceedings of the National Academy of Sciences, vol. 93, No. 22, Oct. 29, 1996, pp. 12287-12291.

Munir, Farasat, "A Fast, Scalable Acoustic Resonator-Based Biosensor Array System for Simultaneous Detection of Multiple Biomarkers," Thesis, Georgia Institute of Technology, Dec. 2012, 160 pages.

Muskal, Nechama et al., "The Electrochemistry of Thiol Self-Assembled Monolayers (SAMs) on a Hanging Mercury Drop Electrode (HMDE)," Current Separations, vol. 19, No. 2, 2000, pp. 49-54.

Nirschl, Martin et al., "CMOS-Integrated Film Bulk Acoustic Resonators for Label-Free Biosensing," Sensors, vol. 10, No. 5, Apr. 27, 2010, pp. 4180-4193.

Yu, Hongyu et al., "Ultra Temperature-Stable Bulk-Acoustic-Wave Resonators with $SiO_2$ Compensation Layer," IEEE: Transactions on Ultrasonics, Ferroelectrics, and Frequency Control, vol. 54, No. 10, Oct. 2007, pp. 2102-2109.

\* cited by examiner

ACOUSTIC RESONATOR DEVICES AND FABRICATION METHODS PROVIDING HERMETICITY AND SURFACE FUNCTIONALIZATION

STATEMENT OF RELATED APPLICATIONS

This application is a non-provisional of U.S. provisional patent application Ser. No. 62/252,402, filed Nov. 6, 2015, the disclosure of which is hereby incorporated herein by reference in its entirety. Subject matter disclosed herein also relates to the following three U.S. patent applications each filed or to be filed on Oct. 26, 2016: (1) U.S. patent application Ser. No. 15/334,511 entitled "Acoustic Resonator Devices and Methods Providing Patterned Functionalization Areas;" (2) U.S. patent application Ser. No. 15/334,482 entitled "Acoustic Resonator Devices and Methods with Noble Metal Layer for Functionalization;" and (3) U.S. patent application Ser. No. 15/334,459 entitled "Acoustic Resonator Device with Controlled Placement of Functionalization Material;" wherein the contents of the foregoing three U.S. patent applications are hereby incorporated by reference as if set forth fully herein.

TECHNICAL FIELD

The present disclosure relates to acoustic resonator devices, including acoustic wave sensors and microfluidic devices suitable for biosensing or biochemical sensing applications.

BACKGROUND

A biosensor (or biological sensor) is an analytical device including a biological element and a transducer that converts a biological response into an electrical signal. Certain biosensors involve a selective biochemical reaction between a specific binding material (e.g., an antibody, a receptor, a ligand, etc.) and a target species (e.g., molecule, protein, DNA, virus, bacteria, etc.), and the product of this highly specific reaction is converted into a measurable quantity by a transducer. Other sensors may utilize a non-specific binding material capable of binding multiple types or classes of molecules or other moieties that may be present in a sample, such as may be useful in chemical sensing applications. The term "functionalization material" may be used herein to generally relate to both specific and non-specific binding materials. Transduction methods may be based on various principles, such as electrochemical, optical, electrical, acoustic, and so on. Among these, acoustic transduction offers a number of potential advantages, such as being real time, label-free, and low cost, as well as exhibiting high sensitivity.

An acoustic wave device employs an acoustic wave that propagates through or on the surface of a piezoelectric material, whereby any changes to the characteristics of the propagation path affect the velocity and/or amplitude of the wave. Presence of functionalization material embodied in a specific binding material along an active region of an acoustic wave device permits a specific analyte to be bound to the specific binding material, thereby altering the mass being vibrated by the acoustic wave and altering the wave propagation characteristics (e.g., velocity, thereby altering resonance frequency). Changes in velocity can be monitored by measuring the frequency, magnitude, or phase characteristics of the sensor, and can be correlated to a physical quantity being measured.

In the case of a piezoelectric crystal resonator, an acoustic wave may embody either a bulk acoustic wave (BAW) propagating through the interior of a substrate, or a surface acoustic wave (SAW) propagating on the surface of the substrate. SAW devices involve transduction of acoustic waves (commonly including two-dimensional Rayleigh waves) utilizing interdigital transducers along the surface of a piezoelectric material, with the waves being confined to a penetration depth of about one wavelength. In a BAW device, three wave modes can propagate, namely, one longitudinal mode (embodying longitudinal waves, also called compressional/extensional waves), and two shear modes (embodying shear waves, also called transverse waves), with longitudinal and shear modes respectively identifying vibrations where particle motion is parallel to or perpendicular to the direction of wave propagation. The longitudinal mode is characterized by compression and elongation in the direction of the propagation, whereas the shear modes consist of motion perpendicular to the direction of propagation with no local change of volume. Longitudinal and shear modes propagate at different velocities. In practice, these modes are not necessarily pure modes as the particle vibration, or polarization, is neither purely parallel nor purely perpendicular to the propagation direction. The propagation characteristics of the respective modes depend on the material properties and propagation direction respective to the crystal axis orientations. The ability to create shear displacements is beneficial for operation of acoustic wave devices with fluids (e.g., liquids) because shear waves do not impart significant energy into fluids.

Certain piezoelectric thin films are capable of exciting both longitudinal and shear mode resonance, such as hexagonal crystal structure piezoelectric materials including (but not limited to) aluminum nitride [AlN] and zinc oxide [ZnO]. To excite a wave including a shear mode using a piezoelectric material layer arranged between electrodes, a polarization axis in a piezoelectric thin film must generally be non-perpendicular to (e.g., tilted relative to) the film plane. In biological sensing applications involving liquid media, the shear component of the resonator is used. In such applications, piezoelectric material may be grown with a c-axis orientation distribution that is non-perpendicular relative to a face of an underlying substrate to enable a BAW resonator structure to exhibit a dominant shear response upon application of an alternating current signal across electrodes thereof.

Typically, BAW devices are fabricated by micro-electro-mechanical systems (MEMS) fabrication techniques owing to the need to provide microscale features suitable for facilitating high frequency operation. In the context of biosensors, functionalization materials (e.g., specific binding materials; also known as bioactive probes or agents) may be deposited on sensor surfaces by microarray spotting (also known as microarray printing) using a microarray spotting needle. Functionalization materials providing non-specific binding utility (e.g., permitting binding of multiple types or species of molecules) may also be used in certain contexts, such as chemical sensing. Unfortunately, the ability to stably operate BAW resonators in the presence of liquid is limited. BAW resonators frequently utilize electrodes composed of reactive metals (e.g., aluminum or aluminum alloy) that are susceptible to corrosion when contacted with liquid. Hypothetical application of material over such electrodes must be carefully considered to avoid excess thickness that could dampen acoustic vibration and result in degraded performance. Surface compatibility of functionalization materials in the vicinity of such electrodes is also a concern, as is cost-effective and repeatable manufacturing.

Accordingly, there is a need for acoustic resonator devices suitable for stable operation in the presence of liquid for biosensing or biochemical sensing applications without negatively impacting device performance.

SUMMARY

The present disclosure provides a micro-electrical-mechanical system (MEMS) resonator device including a passivation structure arranged over a top side electrode of a bulk acoustic wave resonator structure and being suitable for receiving functionalization material (e.g., including but not limited to specific binding material for biological functionalization). The passivation structure includes (i) a hermeticity layer including a dielectric material with a low water vapor transmission rate (e.g., no greater than 0.1 (g/m$^2$/day) and (ii) an interface layer (e.g., a material having a hydroxylated oxide surface, or including gold or another noble metal). The interface layer is preferably configured to receive a self-assembled monolayer (SAM), over which at least one functionalization material may be arranged. An interface layer comprising a hydroxylated oxide surface may receive a SAM comprising an organosilane material, or an interface layer comprising gold or another noble metal may receive a SAM comprising a thiol material, with the SAM being provided between the interface layer and a functionalization material. One or more layers of the passivation structure may advantageously be deposited by atomic layer deposition. The passivation structure beneficially protects the electrode material from attack in corrosive liquid environments while being suitable for proper chemical binding of the SAM that enables functionalization with suitable (e.g., specific binding) material. Methods for fabricating MEMS resonator devices are also provided.

In one aspect, a micro-electrical-mechanical system (MEMS) resonator device includes a substrate, a bulk acoustic wave resonator structure arranged over at least a portion of the substrate and including at least one top side electrode, and multiple layers arranged over the at least one top side electrode. In particular, a hermeticity layer is arranged over at least a portion of the at least one top side electrode; an interface layer is arranged over at least a portion of the hermeticity layer; and at least one functionalization material is arranged over at least a portion of the interface layer, wherein the bulk acoustic wave resonator structure comprises at least one active region below the at least one top side electrode (e.g., corresponding to a portion of a piezoelectric material arranged between overlapping portions of the at least one top side electrode and a corresponding bottom side electrode), and at least a portion of each of the hermeticity layer, the interface layer, and the at least one functionalization material is arranged over the at least one active region. The hermeticity layer preferably includes a dielectric material including a water vapor transmission rate of no greater than 0.1 (g/m$^2$/day). In certain embodiments, the MEMS resonator device further includes a self-assembled monolayer arranged between the interface layer and the at least one functionalization material. In certain embodiments, the interface layer comprises a hydroxylated oxide surface, and the self-assembled monolayer comprises an organosilane material. In certain embodiments, the interface layer comprises gold or another noble metal, and the self-assembled monolayer comprises a thiol material.

In certain embodiments, the hermeticity layer includes an oxide, a nitride, or an oxynitride material (e.g., including but not limited to at least one of Al$_2$O$_3$ or SiN). In certain embodiments, the interface layer comprises at least one of silicon dioxide [SiO$_2$], titanium dioxide [TiO$_2$], tantalum pentoxide [Ta$_2$O$_5$], hafnium oxide [HfO$_2$], or aluminum oxide [Al$_2$O$_3$]. In certain embodiments, the hermeticity layer includes a thickness in a range of from about 5 nm to about 150 nm, from about 5 nm to about 50 nm, or from about 10 nm to about 25 nm, and the interface layer includes a thickness in a range of from about 1 nm to about 50 nm, from about 2 nm to about 20 nm, or from about 5 nm to about 15 nm. In certain embodiments, the at least one top side electrode includes a non-noble metal.

In certain embodiments, the bulk acoustic wave resonator structure includes a hexagonal crystal structure piezoelectric material (e.g., aluminum nitride or zinc oxide) that includes a c-axis having an orientation distribution that is predominantly non-parallel to (and may also be non-perpendicular to) normal of a face of the substrate. In certain embodiments, an acoustic reflector structure is arranged between the substrate and the bulk acoustic wave resonator structure, wherein the bulk acoustic wave resonator structure includes a solidly mounted bulk acoustic wave resonator structure. In certain embodiments, the substrate defines a recess, and the MEMS resonator device further comprises a support layer arranged between the bulk acoustic wave resonator structure and the recess, wherein the at least one active region is arranged over at least a portion of the support layer and at least a portion of the recess (e.g., such as to form a film bulk acoustic wave resonator (FBAR) structure).

Certain embodiments are directed to a sensor including a MEMS resonator device disclosed herein, and/or to a fluidic (e.g., microfluidic) device including a MEMS resonator device disclosed herein and including a fluidic passage arranged to conduct a liquid to contact at least one functionalization material.

In another aspect, a method for biological or chemical sensing includes supplying a fluid containing a target species into the fluidic passage of a fluidic device (e.g., a microfluidic device) as disclosed herein, wherein said supplying is configured to cause at least some of the target species to bind to the at least one functionalization material; inducing a bulk acoustic wave in the at least one active region; and sensing a change in at least one of a frequency property, a magnitude property, or a phase property of the bulk acoustic wave resonator structure to indicate at least one of presence or quantity of target species bound to the at least one functionalization material.

In another aspect, a method for fabricating a micro-electrical-mechanical system (MEMS) resonator device includes multiple steps. Such steps include: forming at least one top side electrode over at least a portion of a piezoelectric material arranged over at least a portion of a substrate; depositing a hermeticity layer over at least a portion of the at least one top side electrode; depositing an interface layer over at least a portion of the hermeticity layer; and depositing at least one functionalization material over at least a portion of the interface layer; wherein the resonator device comprises at least one active region below the at least one top side electrode, and at least a portion of each of the hermeticity layer, the interface layer, and the at least one functionalization material is arranged over the at least one active region. Preferably, the hermeticity layer includes a dielectric material having a water vapor transmission rate of no greater than 0.1 (g/m$^2$/day).

In certain embodiments, the hermeticity layer is deposited by atomic layer deposition. In certain embodiments, the interface layer is deposited by one or more of chemical vapor deposition, atomic layer deposition, or physical vapor deposition. In certain embodiments, atomic layer deposition may be used to deposit both the hermeticity layer and the interface layer. In certain embodiments, the depositing of the interface layer is sequentially performed in a vacuum environment after the depositing of the hermeticity layer.

In certain embodiments, the method further includes forming a self-assembled monolayer over at least a portion of the interface layer prior to deposition of the at least one functionalization material. Preferably the at least one functionalization material is registered with at least a portion of the at least one top side electrode. In certain embodiments, the method further includes depositing a blocking material over a portion of the self-assembled monolayer that is non-coincident with the at least one functionalization material. In certain embodiments, the method further includes depositing an acoustic reflector structure over the substrate, and depositing the piezoelectric material over the acoustic reflector structure. In certain embodiments, the method further includes forming at least one wall over a portion of the interface layer and defining a fluidic passage. Preferably, the fluidic passage may be covered with a cover or cap layer.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosure, and together with the description serve to explain the principles of the disclosure. None of the figures are drawn to scale unless indicated to the contrary herein.

DETAILED DESCRIPTION

Figure 1:
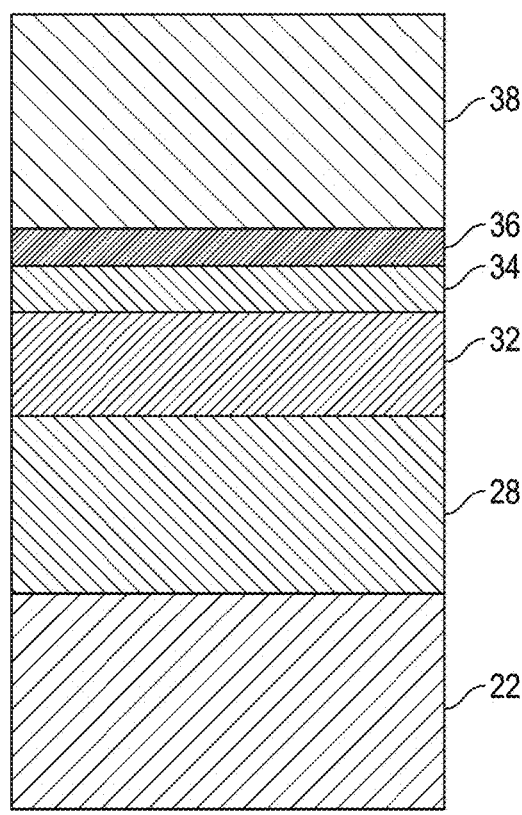
FIG. 1 is a schematic cross-sectional view of an upper portion of a MEMS resonator device according to one embodiment, including a top side electrode overlaid with a hermeticity layer, an interface layer, a self-assembled monolayer, and a functionalization layer (e.g., specific binding material).

Embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof. As used herein, the terms "proximate" and "adjacent" as applied to a specified layer or element refer to a state of being close or near to another layer or element, and encompass the possible presence of one or more intervening layers or elements without necessarily requiring the specified layer or element to be directly on or directly in contact with the other layer or element unless specified to the contrary herein.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

The present disclosure relates in one aspect to a micro-electrical-mechanical system (MEMS) resonator device including a passivation structure arranged over a top side electrode of a bulk acoustic wave resonator structure and being suitable for receiving functionalization material (e.g., including but not limited to specific binding material for biological functionalization). The passivation structure includes (i) a hermeticity layer including a dielectric material with a low water vapor transmission rate (e.g., no greater than 0.1 ($g/m^2$/day)), and (ii) an interface layer (e.g., including a material having a hydroxylated oxide surface, or including gold or another noble metal). In combination, the foregoing hermeticity and interface layers may be considered a bilayer. Following deposition of these layers, a SAM may be formed over the interface layer, with the SAM preferably including an organosilane material or a thiol material, depending on the composition of the interface layer, with the SAM being provided between the interface layer and a functionalization material. The hermeticity layer protects a reactive electrode material (e.g., aluminum or aluminum alloy) from attack in corrosive liquid environments, and the interface layer facilitates proper chemical binding of the SAM.

In certain embodiments, a bulk acoustic wave resonator structure arranged over at least a portion of a substrate includes a piezoelectric material, a top side electrode arranged over a portion of the piezoelectric material, and a bottom side electrode arranged between the piezoelectric material and the substrate, wherein a portion of the piezoelectric material is arranged between the top side electrode and the bottom side electrode to form an active region. In certain embodiments, the piezoelectric material comprises a hexagonal crystal structure piezoelectric material (e.g., aluminum nitride or zinc oxide) that comprises a c-axis having an orientation distribution that is predominantly non-parallel to (and may also be non-perpendicular to) normal of a face of the substrate. Methods for forming hexagonal crystal structure piezoelectric materials including a c-axis having an orientation distribution that is predominantly non-parallel to normal of a face of a substrate are disclosed in U.S. patent application Ser. No. 15/293,063 filed on Oct. 13, 2016, with the foregoing application hereby being incorporated by reference herein. Additional methods for forming piezoelectric materials having an inclined c-axis orientation are disclosed in U.S. Pat. No. 4,640,756 issued on Feb. 3, 1987, with the foregoing patent hereby being incorporated by reference herein.

In certain embodiments, the hermeticity layer and the interface layer may be applied via one or more deposition processes such as atomic layer deposition (ALD), chemical vapor deposition (CVD), or physical vapor deposition (PVD). Of the foregoing processes, ALD is preferred for deposition of at least the hermeticity layer (and may also be preferable for deposition of the interface layer), due to its ability to provide excellent conformal coating with good step coverage over device features, so as to provide layer structures that are free of pinholes. Moreover, ALD is capable of forming uniformly thin layers that provide relatively little damping of acoustic vibrations that would otherwise result in degraded device performance. Adequacy of coverage is important for the hermeticity layer to avoid corrosion of the underlying electrode. If ALD is used for deposition of a hermeticity layer, then in certain embodiments a hermeticity layer may include a thickness in a range of from about 5 nm to about 100 nm, from about 5 nm to about 50 nm, or from about 10 nm to about 25 nm. In certain embodiments, the hermeticity layer thickness is about 15 nm, or from about 12 nm to about 18 nm. Conversely, if another process such as CVD is used, then a hermeticity layer may include a thickness in a range of from about 80 nm to about 150 nm or more, or in a range of from about 80 nm to about 120 nm. Considering both of the foregoing processes, hermeticity layer thicknesses may range from about 5 nm to about 150 nm. If ALD is used for deposition of an interface layer, then an interface layer may include a thickness in a range of from about 5 nm to about 15 nm. In certain embodiments, an interface layer may include a thickness of about 10 nm, or in a range of from about 8 nm to about 12 nm. Other interface layer thickness ranges and/or deposition techniques other than ALD may be used in certain embodiments.

In certain embodiments, a hermeticity layer and an interface layer may be sequentially applied in a vacuum environment, thereby promoting a high-quality interface between the two layers.

In certain embodiments, the hermeticity layer includes an oxide, a nitride, or an oxynitride material serving as a dielectric material and having a low water vapor transmission rate (e.g., no greater than 0.1 ($g/m^2$/day)). In certain embodiments, the hermeticity layer includes at least one of $Al_2O_3$ or SiN. In certain embodiments, the interface layer includes at least one of $SiO_2$, $TiO_2$, or $Ta_2O_5$, $HfO_2$, or $Al_2O_3$. In certain embodiments, multiple materials may be combined in a single hermeticity layer, and/or a hermeticity layer may include multiple sublayers of different materials. Preferably, a hermeticity layer is further selected to promote compatibility with an underlying reactive metal (e.g., aluminum or aluminum alloy) electrode structure of an acoustic resonator structure. Although aluminum or aluminum alloys are frequently used as electrode materials in bulk acoustic wave resonators, various transition and post-transition metals can be used for such electrodes.

In certain embodiments, an interface layer includes a hydroxylated oxide surface suitable for receiving an organosilane-based SAM. A preferred interface layer material including a hydroxylated oxide surface is silicon dioxide [$SiO_2$]. Alternative materials incorporating hydroxylated oxide surfaces include titanium dioxide [$TiO_2$], tantalum pentoxide [$Ta_2O_5$], hafnium oxide [$HfO_2$], or aluminum oxide [$Al_2O_3$]. Other alternative materials incorporating hydroxylated oxide surfaces will be known to those skilled in the art, and these alternatives are considered to be within the scope of the present disclosure.

In other embodiments, an interface layer includes gold or a noble metal suitable for receiving a thiol-based SAM.

Following deposition of an interface layer, a SAM is preferably formed thereover. SAMs are typically formed by exposure of a solid surface to amphiphilic molecules with chemical groups that exhibit strong affinities for the solid surface. When an interface layer comprising a hydroxylated oxide surface is used, then organosilane SAM layers are particularly preferred for attachment to the hydroxylated oxide surface. Organosilane SAMs promote surface bonding through silicon-oxygen (Si—O) bonds. More specifically, organosilane molecules include a hydrolytically sensitive group and an organic group, and are therefore useful for coupling inorganic materials to organic polymers. An organosilane SAM may be formed by exposing a hydroxylated surface to an organosilane material in the presence of trace amounts of water to form intermediate silanol groups. These groups then react with free hydroxyl groups on the hydroxylated oxide surface to covalently immobilize the organosilane. Examples of possible organosilane-based SAMs that are compatible with interface layers incorporating hydroxylated oxide surfaces include 3-glycidoxypropyltrimethoxysilane (GPTMS), 3-mercaptopropyltrimethoxysilane (MPTMS), 3-aminopropyltrimethoxysilane (APTMS), and octadecyltrimethoxysilane (OTMS), including their ethoxy- and chloro-variants. Additional silanes that may be used for SAMs include poly(ethylene glycol) (PEG) conjugated variants. Those skilled in the art will recognize that other alternatives exist, and these alternatives are considered to be within the scope of the present disclosure. An exemplary SAM may include a thickness in a range of at least 0.5 nm or more.

When an interface layer comprising gold or another noble metal is used, then thiol-based (e.g., alkanethiol-based) SAM layers may be used. Alkanethiols are molecules with an alkyl chain as the back bone, a tail group, and a S—H head group. Thiols may be used on noble metal interface layers due to the strong affinity of sulfur for these metals. Examples of thiol-based SAMs that may be used include, but are not limited to, 1-dodecanethiol (DDT), 11-mercaptoundecanoic acid (MUA), and hydroxyl-terminated (hexaethylene glycol) undecanethiol (1-UDT). These thiols contain the same backbone, but different end groups—namely, methyl ($CH_3$), carboxyl (COOH), and hydroxyl-terminated hexaethylene glycol (HO—$(CH_2CH_2O)_6$) for DDT, MUA, and 1-UDT, respectively. In certain embodiments, SAMs may be formed by incubating gold surfaces in thiol solutions using a suitable solvent, such as anhydrous ethanol.

Following formation of a SAM, functionalization (e.g., specific binding or non-specific binding) material may be applied thereover. In certain embodiments, functionalization materials may be applied on or over a SAM using a microarray spotting needle or other suitable methods. Examples of specific binding materials include, but are not limited to, antibodies, receptors, ligands, and the like. A specific binding material is preferably configured to receive a predefined target species (e.g., molecule, protein, DNA, virus, bacteria, etc.). A functionalization layer including specific binding material may include a thickness in a range of from about 5 nm to 1000 nm, or from about 5 nm to about 500 nm. In certain embodiments, an array of different functionalization materials may be provided over different active areas of a multi-resonator device, optionally in combination with one or more active areas that are devoid of functionalization material to serve as comparison (or "reference") regions. In certain embodiments, a functionalization material may provide non-specific binding utility.

Certain embodiments are directed to a fluidic device including one or more multiple bulk acoustic wave MEMS resonator structures as disclosed herein and including a fluidic passage (e.g., a channel, a chamber, or the like) arranged to conduct a liquid to contact at least one functionalization (e.g., specific binding) material arranged over at least one active region of the resonator structures. Such a device may be microfluidic in scale, and comprise at least one microfluidic passage (e.g., having at least one dimension, such as height and/or width, of no greater than about 500 microns, or about 250 microns, or about 100 microns). For example, following fabrication of bulk acoustic wave MEMS resonator structures and deposition of a hermeticity layer and an interface layer (optionally followed by a SAM and at least one functionalization material) over portions thereof, a microfluidic device may be fabricated by forming one or more walls defining lateral boundaries of a microfluidic passage over a first bulk acoustic wave MEMS resonator structure with an active region thereof arranged along a bottom surface of the microfluidic passage, and then enclosing the microfluidic passage using a cover or cap layer that may define fluidic ports (e.g., openings) enabling fluid communication with the microfluidic passages. In certain embodiments, a SAM and/or functionalization (e.g., specific binding) material may be pre-applied to the active region of a bulk acoustic wave MEMS resonator structure before formation of a microfluidic passage; in other embodiments, a SAM and/or functionalization material may be applied over an active region of a bulk acoustic wave resonator structure following formation of the microfluidic passage.

An example of a MEMS resonator device overlaid with multiple layers for providing biosensing utility according to one embodiment is provided in FIG. 1. FIG. 1 is a schematic cross-sectional view of an upper portion of a MEMS resonator device including a piezoelectric material 22 and a top side electrode 28, wherein at least the top side electrode 28 is overlaid with a hermeticity layer 32, an interface layer 34, a self-assembled monolayer 36, and a functionalization layer (e.g., specific binding material) 38. In certain embodiments, the MEMS resonator device includes a bulk acoustic wave resonator device, and the piezoelectric material 22 includes aluminum nitride or zinc oxide material that includes a c-axis having an orientation distribution that is predominantly non-parallel (and may also be non-perpendicular) to normal of a face of the substrate. Such an orientation distribution enables creation of shear displacements, which beneficially enable operation of the MEMS resonator device with liquids, such as in a sensor and/or microfluidic device. In certain embodiments, the piezoelectric material includes a c-axis with a longitudinal orientation.

Figure 2A:
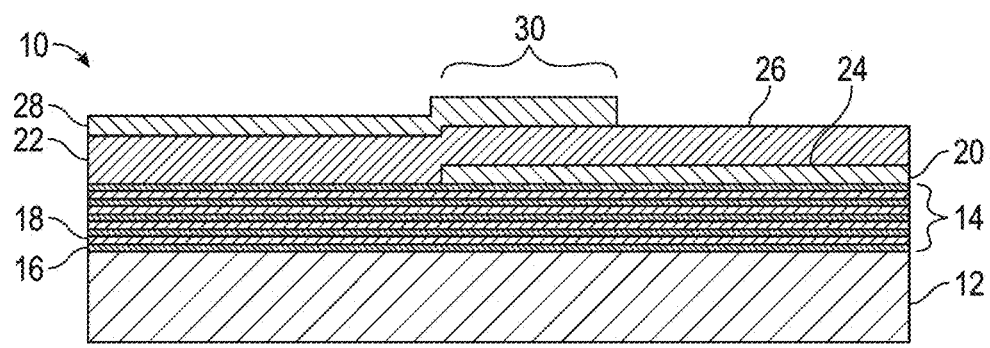
FIG. 2A is a schematic cross-sectional view of a portion of a MEMS resonator device according to another embodiment, including an active region with a piezoelectric material arranged between overlapping portions of a top side electrode and a bottom side electrode.

A representative bulk acoustic wave MEMS resonator device 10 suitable for receiving a passivation structure, a SAM, and at least one functionalization material (e.g., a specific binding material) is shown in FIG. 2A. The device 10 includes a substrate 12 (e.g., typically silicon or another semiconductor material), an acoustic reflector 14 arranged over the substrate 12, a layer of piezoelectric material 22, and bottom and top side electrodes 20, 28. The bottom side electrode 20 is arranged along a portion of a lower surface 24 of the piezoelectric material 22 (between the acoustic reflector 14 and the piezoelectric material 22), and the top side electrode 28 is arranged along a portion of an upper surface 26 of the piezoelectric material 22. An area in which the piezoelectric material 22 is arranged between overlapping portions of the top side electrode 28 and the bottom side electrode 20 is considered the active region 30 of the resonator device 10. At least a portion of each of the hermeticity layer, the interface layer, and the SAM is arranged over the at least one active region. The acoustic reflector 14 serves to reflect acoustic waves and therefore reduce or avoid their dissipation in the substrate 12. In certain embodiments, an acoustic reflector 14 includes alternating thin layers 16, 18 of different materials (e.g., silicon oxicarbide [SiOC], silicon nitride [$Si_3N_4$], silicon dioxide [$SiO_2$], aluminum nitride [AlN], tungsten [W], and molybdenum [Mo]), optionally embodied in a quarter-wave Bragg mirror, deposited over the substrate 12. In certain embodiments, other types of acoustic reflectors may be used. Steps for forming the resonator device 10 may include depositing the acoustic reflector 14 over the substrate 12, followed by deposition of the bottom side electrode 20, followed by growth (e.g., via sputtering or other appropriate methods) of the piezoelectric material 22, followed by deposition of the top side electrode 28.

Figure 2B:
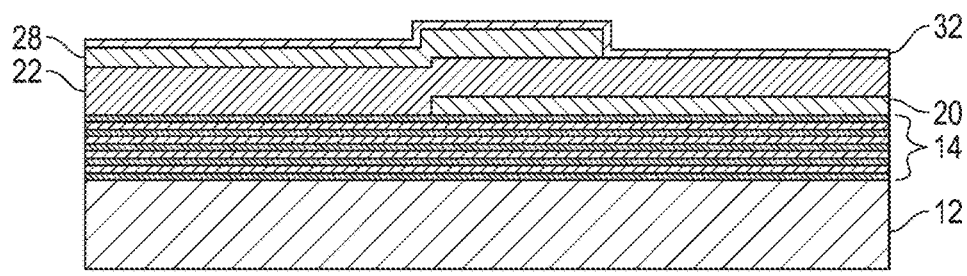
FIG. 2B is a schematic cross-sectional view of the MEMS resonator device of FIG. 2A following deposition of a hermeticity layer over the top side electrode and the piezoelectric material.

FIG. 2B is a schematic cross-sectional view of the MEMS resonator device 10 of FIG. 2A following deposition of a hermeticity layer 32 over the top side electrode 28 and portions of the piezoelectric material 22. The hermeticity layer 32 preferably includes a dielectric material with a low water vapor transmission rate (e.g., no greater than 0.1 (g/m$^2$/day). In certain embodiments, the hermeticity layer 32 includes an oxide, a nitride, or an oxynitride material, such as (but not limited to) one or more of $Al_2O_3$, or $SiO_2$.

Figure 2C:
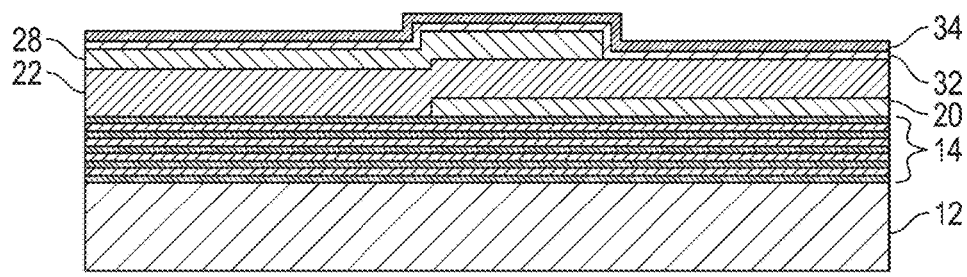
FIG. 2C is a schematic cross-sectional view of the MEMS resonator device of FIG. 2B following deposition of an interface layer over the hermeticity layer.

FIG. 2C is a schematic cross-sectional view of the coated MEMS resonator device of FIG. 2B following deposition of an interface layer 34 over the hermeticity layer 32. The interface layer 34 includes a hydroxylated oxide surface, and in certain embodiments may comprise one or more of silicon dioxide [$SiO_2$], titanium dioxide [$TiO_2$], tantalum pentoxide [$Ta_2O_5$], hafnium oxide [$HfO_2$], or aluminum oxide [$Al_2O_3$].

Figure 2D:
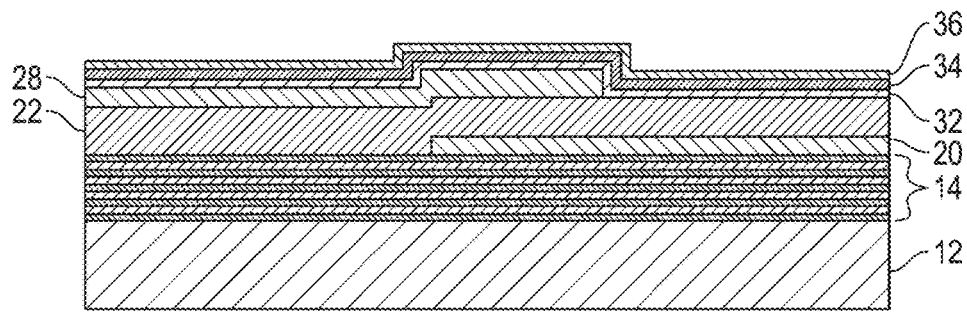
FIG. 2D is a schematic cross-sectional view of the MEMS resonator device of FIG. 2C following formation of a self-assembled monolayer over the interface layer.

FIG. 2D is a schematic cross-sectional view of the coated MEMS resonator device of FIG. 2C following formation of a self-assembled monolayer (SAM) 36 over the interface layer 34. In certain embodiments, the SAM includes an organosilane material. Examples of suitable SAM materials include GPTMS, MPTMS, APTMS, OTMS, and PEG organosilanes. Other examples of organosilane SAM materials and methods for their formation are well known to those skilled in the art. In other embodiments, the SAM includes a thiol material.

Figure 2E:
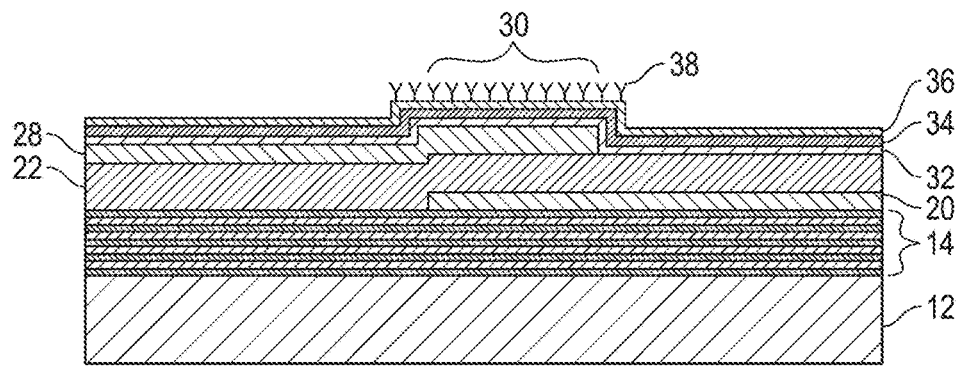
FIG. 2E is a schematic cross-sectional view of the MEMS resonator device of FIG. 2D following application of functionalization material to a portion of the self-assembled monolayer to overlap an active region of the MEMS resonator device.

FIG. 2E is a schematic cross-sectional view of the MEMS resonator device of FIG. 2D following application of functionalization material 38 to a portion of the self-assembled monolayer 36 to overlap an active region 30 of the resonator device. As shown, the functionalization material 38 overlaps the active region 30 of the device. The device of FIG. 2E may be used as a sensor to detect presence of a target species in an environment. When an acoustic wave is induced in the active region 30, and functionalization material 38 is exposed to a target species that binds to the functionalization material 38, a change in one or more wave propagation properties (e.g., frequency, magnitude, and/or phase characteristics) of the device may be detected to indicate presence and/or quantity of target species in the environment.

In certain embodiments, a blocking layer may be arranged (e.g., patterned) over regions of a SAM in which a functionalization (e.g., specific binding) material is not present or not desired, with a blocking layer being useful to prevent non-specific binding of non-target species to a SAM. Examples of blocking materials that may be used include non-oxide thin films such as silicon nitride [SiN] or silicon carbide [SiC]; organic materials such as SU8, photoresist, polyimide, parylene, or poly(ethylene glycol) [PEG]; or chemical or biological buffers or proteins (such as bovine serum albumin (BSA)).

Certain embodiments are directed to a microfluidic device including a MEMS resonator device disclosed herein and including a fluidic passage arranged to conduct a liquid to contact at least one functionalization material. For example, following fabrication of a MEMS resonator device and application of a passivation structure (e.g., hermeticity layer and interface layer) and SAM thereover, a fluidic device may be fabricated by forming one or more walls defining lateral boundaries of a microfluidic channel preferably containing the active region of at least one acoustic resonator, followed by application of a cover or cap layer to enclose the microfluidic channel. In certain embodiments, functionalization (e.g., specific binding) material may be applied following formation of walls of a microfluidic channel, but prior to application of the cover or cap layer.

Figure 3A:
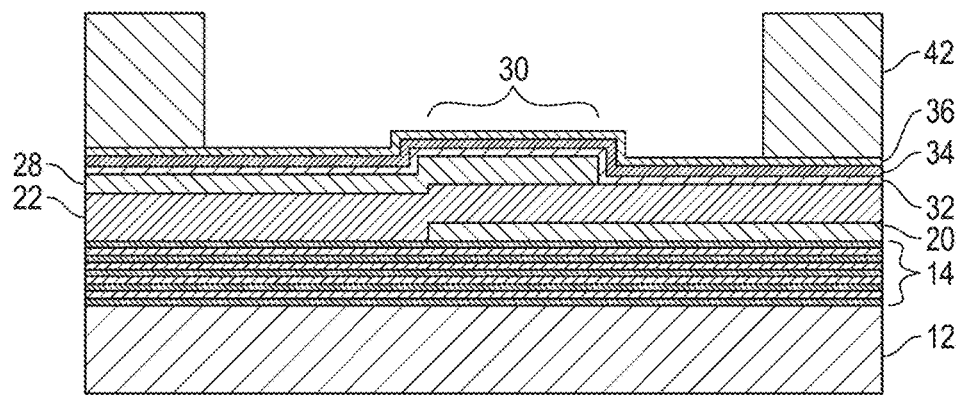
FIG. 3A is a schematic cross-sectional view of the MEMS resonator device of FIG. 2D following formation of walls to define lateral boundaries of a microfluidic channel containing the active region of the MEMS resonator device.

FIGS. 3A-3D illustrate formation of a fluidic device including a bulk acoustic wave MEMS resonator device. FIG. 3A is a schematic cross-sectional view of the MEMS resonator device of FIG. 2D following formation of walls 42 to define lateral boundaries of a microfluidic channel containing the active region of the MEMS resonator device. The MEMS resonator device includes a substrate 12, an acoustic reflector 14 arranged over the substrate 12, a layer of piezoelectric material 22, and bottom and top side electrodes 20, 28 arranged under and over regions of the piezoelectric material 22, respectively. An area in which the piezoelectric material 22 is arranged between overlapping portions of the top side electrode 28 and the bottom side electrode 20 defines an active region 30. A hermeticity layer 32 is provided over the top side electrode 28 and the piezoelectric material 22, an interface layer 34 is arranged over the hermeticity layer 32, and a SAM 36 is provided over the interface layer 34. Walls 42 that are laterally displaced from the active region 30 extend upward from the SAM 36 to define lateral boundaries of a microfluidic channel containing the active region 30. Such walls may be formed of any suitable material, such as SU-8 negative epoxy resist, other photoresist material, or laser-cut "stencil" layers of thin polymeric materials optionally including one or more self-adhesive surfaces (e.g., adhesive tape). Optionally such walls 42 may be formed prior to deposition of a SAM and functionalization and blocking layers with an SU-8 negative epoxy resist or other photoresist material.

Figure 3B:
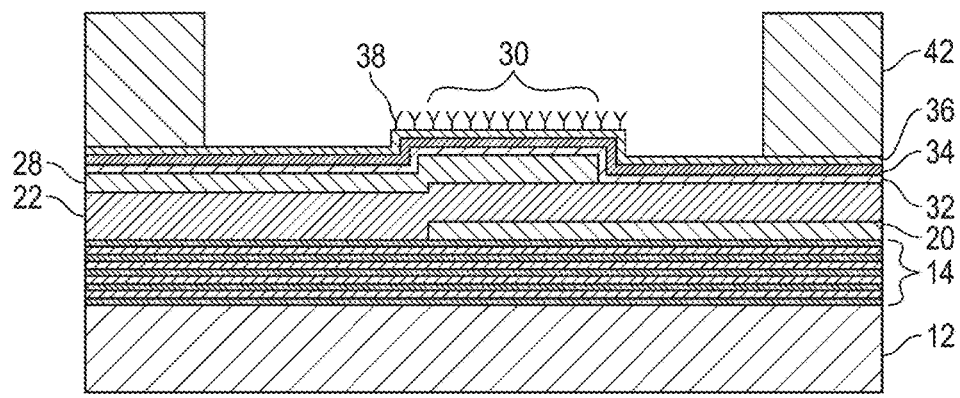
FIG. 3B is a schematic cross-sectional view of the device of FIG. 3A following application of functionalization material to a portion of the self-assembled monolayer to overlap the active region of the MEMS resonator device.

FIG. 3B is a schematic cross-sectional view of the device of FIG. 3A following application of functionalization (e.g., specific binding) material 38 to a portion of the SAM 36 to overlap the active region 30 of the resonator device. In certain embodiments, the functionalization material 38 may be applied on or over the SAM 36 using a microarray spotting needle or other suitable methods, with the functionalization material 38 preferably overlapping the active region 30.

Figure 3C:
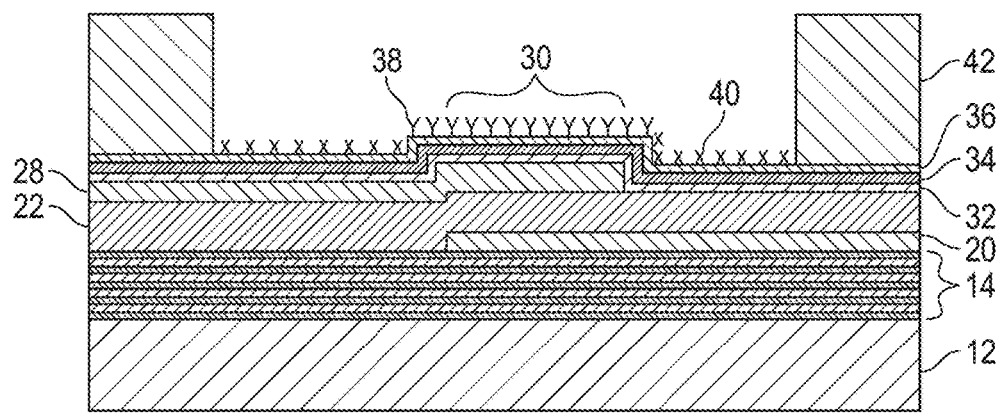
FIG. 3C is a schematic cross-sectional view of the device of FIG. 3B following application of a blocking material over portions of the self-assembled monolayer non-coincident with the active region.

FIG. 3C is a schematic cross-sectional view of the device of FIG. 3B following application of a blocking material 40 over portions of the SAM 36 non-coincident with the active region 30. An example of a suitable blocking material may include bovine serum albumin (BSA).

Figure 3D:
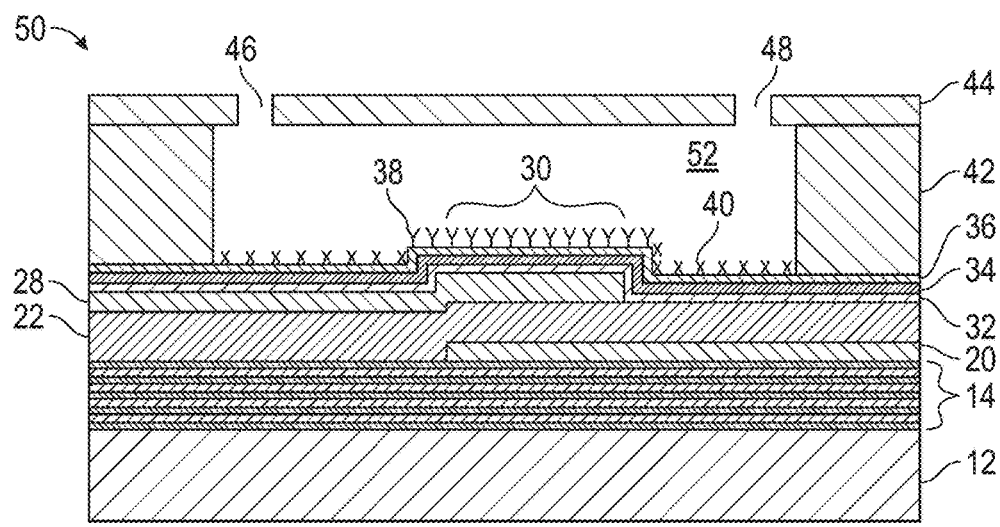
FIG. 3D is a schematic cross-sectional view of the device of FIG. 3C following application of a cover or cap layer over the walls to enclose a microfluidic channel containing the active region of the MEMS resonator device.

FIG. 3D is a schematic cross-sectional view of the device of FIG. 3C following application of a cover or cap layer 44 over the walls 42 to yield a microfluidic device 50 including an enclosed microfluidic channel 52 containing the active region 30 overlaid with functionalization material 38. The cover or cap layer 44 includes ports 46, 48 that may be used to supply fluid (e.g., liquid) into the microfluidic channel 52. The cover or cap layer 44 may embody any suitable material compatible with the fluid, and the cover or cap layer 44 may be optically transmissive in certain embodiments. Examples of desirable materials for the cover or cap layer 44 include, but are not limited to, polymeric materials such as polypropylene, polyethylene, polycarbonate, and the like, or inorganic, nonmetallic materials such as ceramics or glasses. In use of the microfluidic device 50, liquid may be supplied through one of the ports 46, 48 into the microfluidic channel 52 to contact the functionalization material 38. When an acoustic wave is induced in the active region 30, and target species contained in liquid supplied to the microfluidic channel 52 binds with the functionalization material 38, a change in one or more wave propagation properties (e.g., frequency, magnitude, and/or phase characteristics) of the MEMS resonator device may be detected to indicate presence and/or quantity of target species in the liquid. Presence of the hermeticity layer 32 prevents the liquid from corroding the top side electrode 28, while the interface layer 34 facilitates attachment of the SAM 36 that enables application of the functionalization material 38.

Figure 4:
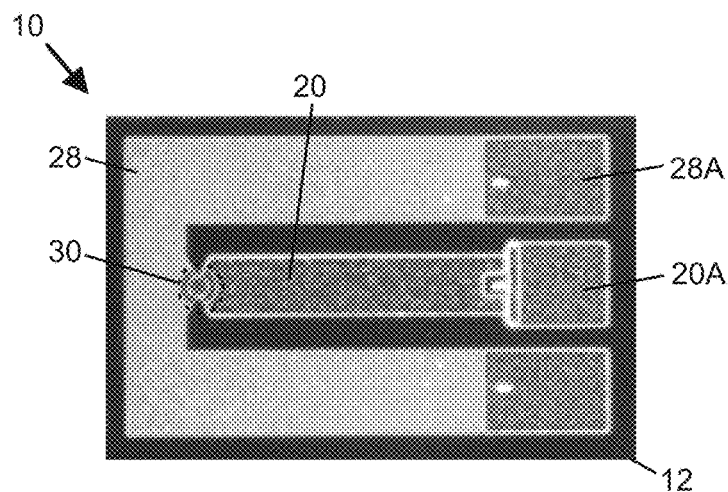
FIG. 4 is a top plan view photograph of a bulk acoustic wave MEMS resonator device suitable for receiving a hermeticity layer, an interface layer, a self-assembled monolayer, and functionalization (e.g. specific binding) material as disclosed herein.

FIG. 4 is a top plan view photograph of a bulk acoustic wave MEMS resonator device 10 (consistent with the device 10 illustrated in FIG. 2A) suitable for receiving a hermeticity layer, an interface layer, a self-assembled monolayer, and functionalization (e.g., specific binding) material as disclosed herein. The MEMS resonator device 10 includes a piezoelectric material (not shown) arranged over a substrate 12, a bottom side electrode 20 arranged under a portion of the piezoelectric material, and a top side electrode 28 arranged over a portion of the piezoelectric material, including an active region 30 in which the piezoelectric material is arranged between overlapping portions of the top side electrode 28 and the bottom side electrode 20. Externally accessible contacts 20A, 28A are in electrical communication with the bottom side electrode 20 and the top side electrode 28, respectively. After the MEMS resonator device 10 is overlaid with an interface layer, a self-assembled monolayer, and functionalization (e.g., specific binding) material as disclosed herein, the device 10 may be used as a sensor and/or incorporated into a microfluidic device. If desired, multiple MEMS resonator devices 10 may be provided in an array on a single substrate 12.

Figure 5:
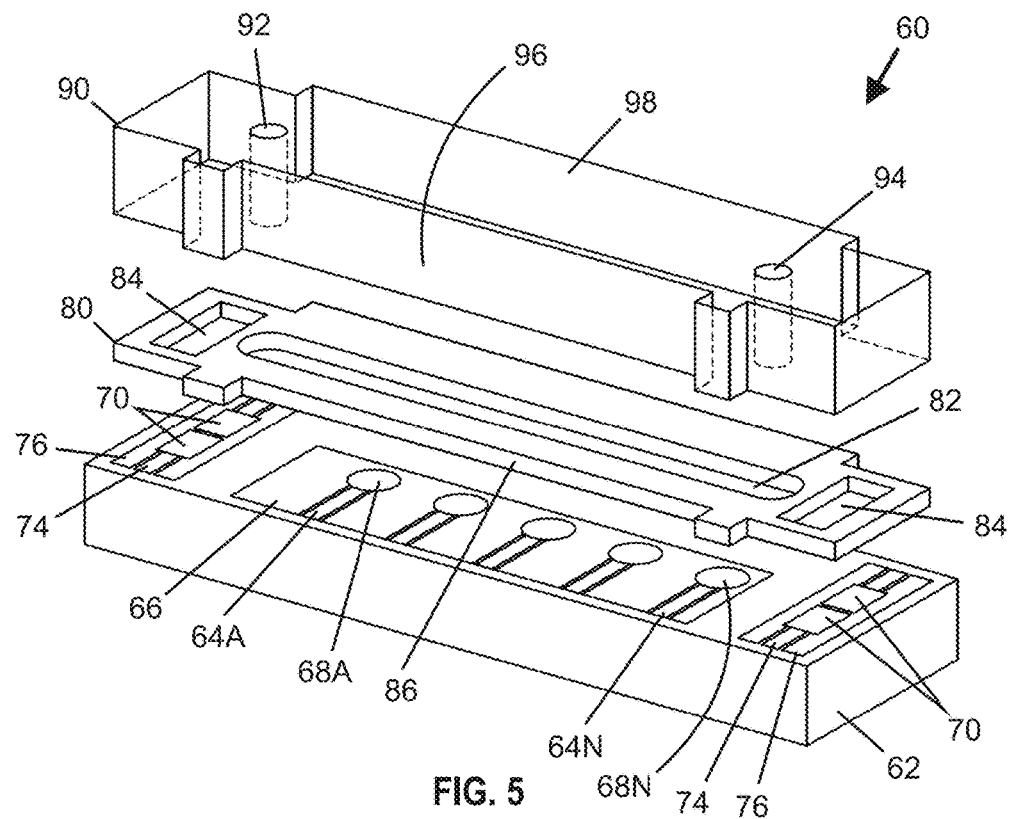
FIG. 5 is a perspective assembly view of a microfluidic device incorporating a substrate with multiple bulk acoustic wave MEMS resonator devices, an intermediate layer defining a channel containing active regions of the MEMS resonator devices, and a cover layer.

FIG. 5 is a perspective assembly view of a microfluidic device 60 incorporating a substrate 62 with multiple bulk acoustic wave MEMS resonator devices, an intermediate layer 80 defining a central microfluidic channel 82 registered with active regions 68A-68N of the MEMS resonator devices, and a cover or cap layer 90 arranged to cover the intermediate layer 80. Top central portions of the substrate 62, which includes an acoustic reflector (not shown) and a piezoelectric material (not shown), include a top side electrode 66 and bottom side electrodes 64A-64N. Regions in which the foregoing electrodes overlap one another and encompass the piezoelectric material embody active regions 68A-68N. Any suitable number of active regions 68A-68N may be provided and fluidically arranged in series or parallel, although five are illustrated in FIG. 5. Top peripheral (or top end) portions of the substrate 62 further include reference top side electrodes 76 and reference bottom side electrodes 74 in communication with reference overlap regions 70. Such reference overlap regions 70 are not exposed to fluid, and are present to provide a basis for comparing signals obtained from the active regions 68A-68N exposed to fluid within the central microfluidic channel 82. The substrate 62 is overlaid with the intermediate layer 80, wherein the central microfluidic channel 82 is intended to receive fluid, and defines peripheral chambers 84 arranged to overlie the reference overlap regions 70 in a sealed fashion. The intermediate layer 80 may be formed of any suitable material such as SU-8 negative epoxy resist, other photoresist material, or laser-cut "stencil" layers of thin polymeric materials optionally including one or more self-adhesive surfaces (e.g., adhesive tape), etc. The intermediate layer 80 further includes a lateral inset region 86 that enables lateral portions of the top side electrode 66 and bottom side electrodes 64A-64N to be accessed upon assembly of the microfluidic device 60. The cover or cap layer 90 includes a lateral inset region 96 registered with the lateral inset region 86 of the intermediate layer 80, and includes microfluidic ports 92, 94 accessible along a top surface 98 and registered with end portions of the central microfluidic channel 82 defined in the intermediate layer 80 to permit fluid (e.g., liquid) to be supplied to the central microfluidic channel 82 over the active regions 68A-68N. Preferably, at least the electrodes 64A-64N, 66 are overlaid with a hermeticity layer, an interface layer, a self-assembled monolayer, and functionalization (e.g., specific binding) material as disclosed herein. Microfluidic devices according to other configurations may be provided, as will be recognized by those skilled in the art upon review of the present disclosure.

Figure 6:
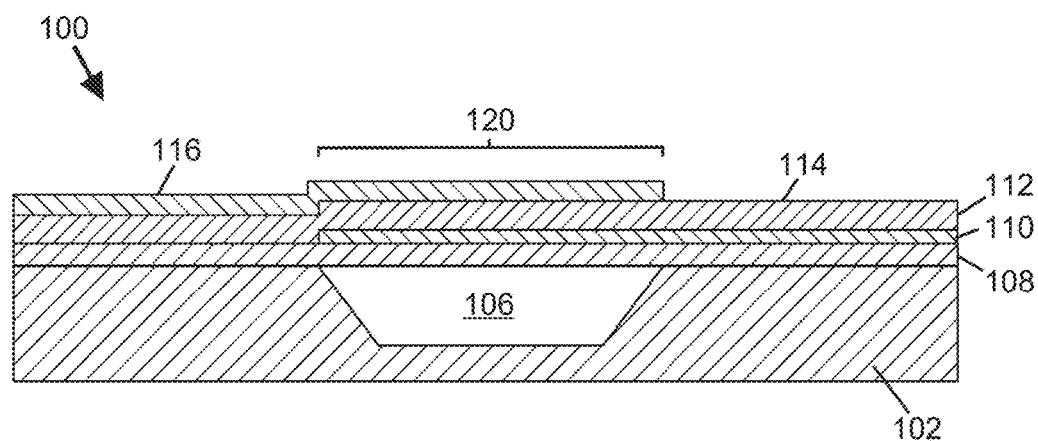
FIG. 6 is a schematic cross-sectional view of a film bulk acoustic wave resonator (FBAR) structure usable in devices according to certain embodiments, with the FBAR structure including an inclined c-axis hexagonal crystal structure piezoelectric material, a substrate defining a cavity covered by a support layer, and an active region registered with the cavity with a portion of the piezoelectric material arranged between overlapping portions of a top side electrode and a bottom side electrode.

FIG. 6 is a schematic cross-sectional view of a film bulk acoustic wave resonator (FBAR) structure 100 including an active region, with at least portions of the FBAR structure 100 subject to being overlaid with an interface layer and a self-assembled monolayer (SAM) suitable for receiving a functionalization material (e.g., specific binding or non-specific binding material), according to one embodiment. The FBAR structure 100 includes a substrate 102 (e.g., silicon or another semiconductor material) defining a cavity 106 that is covered by a support layer 108 (e.g., silicon dioxide). A bottom side electrode 110 is arranged over a portion of the support layer 108, a piezoelectric material layer 112, preferably embodying inclined c-axis hexagonal crystal structure piezoelectric material (e.g., AlN or ZnO), is arranged over the bottom side electrode 110 and the support layer 108, and a top side electrode 116 is arranged over at least a portion of a top surface 114 of the piezoelectric material layer 112. A portion of the piezoelectric material layer 112 arranged between the top side electrode 116 and the bottom side electrode 110 embodies an active region 120 of the FBAR structure 100. The active region 120 is arranged over and registered with the cavity 106 disposed below the support layer 108. The cavity 106 serves to confine acoustic waves induced in the active region 120 by preventing dissipation of acoustic energy into the substrate 102, since acoustic waves do not efficiently propagate across the cavity 106. In this respect, the cavity 106 provides an alternative to the acoustic reflector 14 illustrated in FIGS. 2A-3D. Although the cavity 106 shown in FIG. 6 is bounded from below by a thinned portion of the substrate 102, in alternative embodiments at least a portion of the cavity 106 may extend through an entire thickness of the substrate 102. Steps for forming the FBAR structure 100 may include defining the cavity 106 in the substrate 102, filling the cavity 106 with a sacrificial material (not shown) optionally followed by planarization of the sacrificial material, depositing the support layer 108 over the substrate 102 and the sacrificial material, removing the sacrificial material (e.g., by flowing an etchant through vertical openings defined in the substrate 102 or the support layer 108, or lateral edges of the substrate 102), depositing the bottom side electrode 110 over the support layer 108, growing (e.g., via sputtering or other appropriate methods) the piezoelectric material layer 112, and depositing the top side electrode 116.

As will be recognized by one skilled in the art upon review of the present disclosure, in certain embodiments the FBAR structure 100 of FIG. 6 may be substituted for solidly mounted BAW structures as disclosed in FIGS. 2A-3D, with at least portions of the bulk acoustic wave structures being overlaid with an interface layer and a self-assembled monolayer suitable for receiving a functionalization material (e.g., specific binding or non-specific binding material), Those skilled in the art will recognize improvements and modifications to the preferred embodiments of the present disclosure. All such improvements and modifications are considered within the scope of the concepts disclosed herein and the claims that follow.

What is claimed is:

1. A micro-electrical-mechanical system (MEMS) resonator device comprising:
    a substrate;
    a bulk acoustic wave resonator structure arranged over at least a portion of the substrate, the bulk acoustic wave resonator structure including at least one top side electrode;
    a hermeticity layer arranged over at least a portion of the at least one top side electrode, the hermeticity layer comprising a dielectric material including a water vapor transmission rate of no greater than 0.1 (g/m$^2$/day);
    an interface layer arranged over at least a portion of the hermeticity layer; and
    at least one functionalization material arranged over at least a portion of the interface layer;
    wherein the bulk acoustic wave resonator structure comprises at least one active region below the at least one top side electrode, and at least a portion of each of the hermeticity layer, the interface layer, and the at least one functionalization material is arranged over the at least one active region.

2. The MEMS resonator device of claim 1, further comprising a self-assembled monolayer arranged between the interface layer and the at least one functionalization material.

3. The MEMS resonator device of claim 2, wherein the interface layer comprises a hydroxylated oxide surface, and the self-assembled monolayer comprises an organosilane material.

4. The MEMS resonator device of claim 2, wherein the interface layer comprises gold or another noble metal, and the self-assembled monolayer comprises a thiol material.

5. The MEMS resonator device of claim 1, wherein the hermeticity layer comprises an oxide, a nitride, or an oxynitride material.

6. The MEMS resonator device of claim 1, wherein the interface layer comprises at least one of $SiO_2$, $TiO_2$, $Ta_2O_5$, $HfO_2$, or $Al_2O_3$.

7. The MEMS resonator device of claim 1, wherein the at least one top side electrode comprises a non-noble metal.

8. The MEMS resonator device of claim 1, wherein the hermeticity layer comprises a thickness in a range of from about 5 nm to about 150 nm, and the interface layer comprises a thickness in a range of from about 5 nm to about 15 nm.

9. The MEMS resonator device of claim 1, wherein the bulk acoustic wave resonator structure comprises a hexagonal crystal structure piezoelectric material that comprises a c-axis having an orientation distribution that is predominantly non-parallel to normal of a face of the substrate.

10. The MEMS resonator device of claim 1, further comprising an acoustic reflector structure arranged between the substrate and the bulk acoustic wave resonator structure, wherein the bulk acoustic wave resonator structure comprises a solidly mounted bulk acoustic wave resonator structure.

11. The MEMS resonator device of claim 1, wherein the substrate defines a recess, a support layer is provided between the bulk acoustic wave resonator structure and the recess, and the at least one active region is arranged over at least a portion of the support layer and at least a portion of the recess.

12. A sensor comprising the MEMS resonator device of claim 1.

13. A fluidic device comprising the MEMS resonator device of claim 1, and a fluidic passage arranged to conduct a liquid to contact the at least one functionalization material.

14. A method for biological or chemical sensing, the method comprising:
    supplying a fluid containing a target species into the fluidic passage of the fluidic device according to claim 13, wherein said supplying is configured to cause at least some of the target species to bind to the at least one functionalization material;
    inducing a bulk acoustic wave in the at least one active region; and
    sensing a change in at least one of a frequency property, a magnitude property, or a phase property of the bulk acoustic wave resonator structure to indicate at least one of presence or quantity of target species bound to the at least one functionalization material.

15. A method for fabricating a micro-electrical-mechanical system (MEMS) resonator device, the method comprising:
    forming at least one top side electrode over at least a portion of a piezoelectric material arranged over at least a portion of a substrate;
    depositing a hermeticity layer over at least a portion of the at least one top side electrode, the hermeticity layer comprising a dielectric material including a water vapor transmission rate of no greater than 0.1 (g/m$^2$/day);
    depositing an interface layer over at least a portion of the hermeticity layer; and
    depositing at least one functionalization material over at least a portion of the interface layer;
    wherein the resonator device comprises at least one active region below the at least one top side electrode, and at least a portion of each of the hermeticity layer, the interface layer, and the at least one functionalization material is arranged over the at least one active region.

16. The method of claim 15, wherein the depositing of the hermeticity layer comprises atomic layer deposition, and the depositing of the interface layer comprises at least one of chemical vapor deposition, atomic layer deposition, or physical vapor deposition.

17. The method of claim 15, wherein the depositing of the interface layer is sequentially performed in a vacuum environment after the depositing of the hermeticity layer.

18. The method of claim 15, further comprising forming a self-assembled monolayer over at least a portion of the interface layer prior to deposition of the at least one functionalization material.

19. The method of claim 18, further comprising depositing a blocking material over a portion of the self-assembled monolayer that is non-coincident with the at least one functionalization material.

20. The method of claim 15, further comprising forming at least one wall over a portion of the interface layer and defining a fluidic passage.

\* \* \* \* \*